(12) United States Patent
Varadarajan et al.

(10) Patent No.: US 10,699,290 B1
(45) Date of Patent: Jun. 30, 2020

(54) SYSTEM FOR PROCESSING A SUPPLEMENTAL NUTRITION ASSISTANCE PROGRAM AND RELATED METHODS

(71) Applicant: INMAR GOVERNMENT SERVICES, LLC, Winston-Salem, NC (US)

(72) Inventors: Srinivasan Varadarajan, Winston-Salem, NC (US); Gregory L. Kerr, Winston-Salem, NC (US); L. David Mounts, Winston-Salem, NC (US)

(73) Assignee: INMAR GOVERNMENT SERVICES, LLC, Winston-Salem, NC (US)

( * ) Notice: Subject to any disclaimer, the term of this patent is extended or adjusted under 35 U.S.C. 154(b) by 267 days.

(21) Appl. No.: 15/705,357

(22) Filed: Sep. 15, 2017

(51) Int. Cl.
*G06Q 30/02* (2012.01)
*G06Q 20/36* (2012.01)
*G16H 50/30* (2018.01)

(52) U.S. Cl.
CPC ..... *G06Q 30/0238* (2013.01); *G06Q 30/0207* (2013.01); *G06Q 20/36* (2013.01); *G16H 50/30* (2018.01)

(58) Field of Classification Search
CPC .................................................. G06Q 20/227
See application file for complete search history.

(56) References Cited

U.S. PATENT DOCUMENTS

| | | | |
|---|---|---|---|
| 10,402,804 B1* | 9/2019 | Wittern, III | G06Q 20/204 |
| 2014/0279474 A1* | 9/2014 | Evans | G06Q 20/3572 705/41 |
| 2015/0206450 A1* | 7/2015 | Wayman | G09B 5/02 434/127 |
| 2016/0063532 A1* | 3/2016 | Loeb | G06Q 20/209 705/14.25 |
| 2016/0148244 A1* | 5/2016 | Nordstrand | G06Q 30/0238 705/14.38 |
| 2016/0314531 A1* | 10/2016 | Dangott | G06Q 40/02 |
| 2016/0379520 A1* | 12/2016 | Borel | G09B 19/0092 434/127 |

\* cited by examiner

*Primary Examiner* — John Van Bramer
*Assistant Examiner* — Brendon Beheshti
(74) *Attorney, Agent, or Firm* — Allen, Dyer, Doppelt + Gilchrist, P.A.

(57) ABSTRACT

A system for processing a supplemental nutrition assistance program (SNAP) may include a point-of-sale (POS) terminal and a SNAP administration server coupled to the POS terminal. The SNAP administration server may store SNAP eligible products, and store SNAP payment wallets each associated with a SNAP user and each having an associated credit value to be used toward purchase of the SNAP eligible products. The SNAP administration server may also store SNAP coupon wallets each associated with the SNAP user and each having an associated digital coupon value to be used toward the purchase of SNAP eligible products. The SNAP administration server may further determine whether products being purchased match the SNAP eligible products and, for each matching product, apply the associated digital coupon value and apply the associated credit value toward the purchase at the POS terminal.

22 Claims, 6 Drawing Sheets

SYSTEM FOR PROCESSING A SUPPLEMENTAL NUTRITION ASSISTANCE PROGRAM AND RELATED METHODS

TECHNICAL FIELD

The present invention relates to the field of electronics, and, more particularly, to processing a supplemental nutrition assistance program and related methods.

BACKGROUND

The supplemental nutrition assistance program (SNAP) is a government funded program that offers nutrition assistance to eligible, low-income individuals and families. The nutrition assistance may be in the form of an electronic benefits transfer (EBT) card that may be used at grocery stores or eligible food stores toward eligible products.

Benefits paid out through SNAP exceed $70 billion per year and are received by over 44 million people in the United States. While an average household collects over $100 in monthly benefits, the amount of SNAP benefits received by a household generally depends on the size, income, and expenses of a given household.

A problem that faces SNAP is fraud. More particularly, benefits under SNAP may be diverted from those low-income families and may often be converted to cash. Fraud may also occur in the administration of SNAP, which may add to the overall costs of the program in addition to the general administrative costs.

U.S. Patent Application Publication No. 2016/0063532 to Loeb et al. is directed to a system for incentivizing healthy food purchasing. More particularly, the system may process food purchase receipts that represent purchases via SNAP. Receipts for SNAP purchases may be identified by the system and additional incentive data/rules may be applicable to such purchases. For example, the incentive rules applicable to SNAP purchases may provide additional incentives to promote cost-effective purchasing habits directed toward healthy eating choices.

SUMMARY

A system for processing a supplemental nutrition assistance program (SNAP) may include a point-of-sale (POS) terminal and a SNAP administration server coupled to the POS terminal and that includes a processor and a memory. The processor and the memory cooperate to store, in the memory, a plurality of SNAP eligible products and store, in the memory, a plurality of SNAP payment wallets each associated with a respective given SNAP user and each having an associated credit value to be used toward purchase of the plurality of SNAP eligible products. The processor and the memory cooperate to store, in the memory, a plurality of SNAP coupon wallets each associated with the respective given SNAP user and each having an associated digital coupon value to be used toward the purchase of respective ones of the plurality of SNAP eligible products. The processor and the memory further cooperate to determine whether products being purchased match the plurality of SNAP eligible products and for each of the products being purchased that match the plurality of SNAP eligible products, apply the associated digital coupon value from the corresponding SNAP coupon wallet and apply the associated credit value from the corresponding SNAP payment wallet toward the purchase at the POS terminal.

The POS terminal may be configured to scan the products being purchased during a purchase transaction. The POS terminal may be configured to communicate the products being purchased during the purchase transaction to the SNAP administration server, for example. The POS terminal may be configured to communicate the products being purchased on a per-item basis, for example.

The plurality of SNAP eligible products may be for a plurality of geographic locations. The processor and memory may cooperate to determine a geographic location of the POS terminal and determine whether the products being purchased match the plurality of SNAP eligible products based upon the geographic location, for example.

Each of the plurality of SNAP eligible products may have a health score associated therewith based upon its respective nutritional value. The processor may be configured to generate a combined health score for the products being purchased that match the plurality of SNAP eligible products, for example.

The processor may be configured to cooperate with the memory to authenticate the given SNAP user based upon the POS terminal. The system may further include a mobile wireless communications device communicating with the SNAP administration server. The processor may be configured to authenticate the given SNAP user based upon the mobile wireless communication device, for example. The processor may be configured to communicate a notification to the mobile wireless communications device including a total value of the purchase of the plurality of SNAP eligible products and the associated credit value after the purchase of the plurality of SNAP eligible products, for example.

A method aspect is directed to a method of processing a SNAP. The method may include using a SNAP administration server that includes a processor and a memory cooperating therewith to store, in the memory, a plurality of SNAP eligible products and store, in the memory, a plurality of SNAP payment wallets each associated with a respective given SNAP user and each having an associated credit value to be used toward purchase of the plurality of SNAP eligible products. The method may also include using the SNAP administration server to store, in the memory, a plurality of SNAP coupon wallets each associated with the respective given SNAP user and each having an associated digital coupon value to be used toward the purchase of respective ones of the plurality of SNAP eligible products. The method may also include using the SNAP administration server to determine whether products being purchased match the plurality of SNAP eligible products. The method may also include, for each of the products being purchased that match the plurality of SNAP eligible products, using the SNAP administration server to apply the associated digital coupon value from the corresponding SNAP coupon wallet and apply the associated credit value from the corresponding SNAP payment wallet toward the purchase at the POS terminal.

A computer readable medium aspect is directed to a non-transitory computer readable medium that includes computer-executable instructions that cause a processor of a SNAP administration server to perform operations. The operations may include storing, in the memory, a plurality of SNAP eligible products and storing, in the memory, a plurality of SNAP payment wallets each associated with a respective given SNAP user and each having an associated credit value to be used toward purchase of the plurality of SNAP eligible products. The operations may also include storing, in the memory, a plurality of SNAP coupon wallets each associated with the respective given SNAP user and each having an associated digital coupon value to be used toward the purchase of respective ones of the plurality of SNAP eligible products, and determining products being purchased from a POS terminal. The operations may further include determining whether the products being purchased match the plurality of SNAP eligible products and for each of the products being purchased that match the plurality of SNAP eligible products, applying the associated digital coupon value from the corresponding SNAP coupon wallet and applying the associated credit value from the corresponding SNAP payment wallet toward the purchase at the POS terminal.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple notation is used to indicate similar elements in alternative embodiments.

Figure 1:
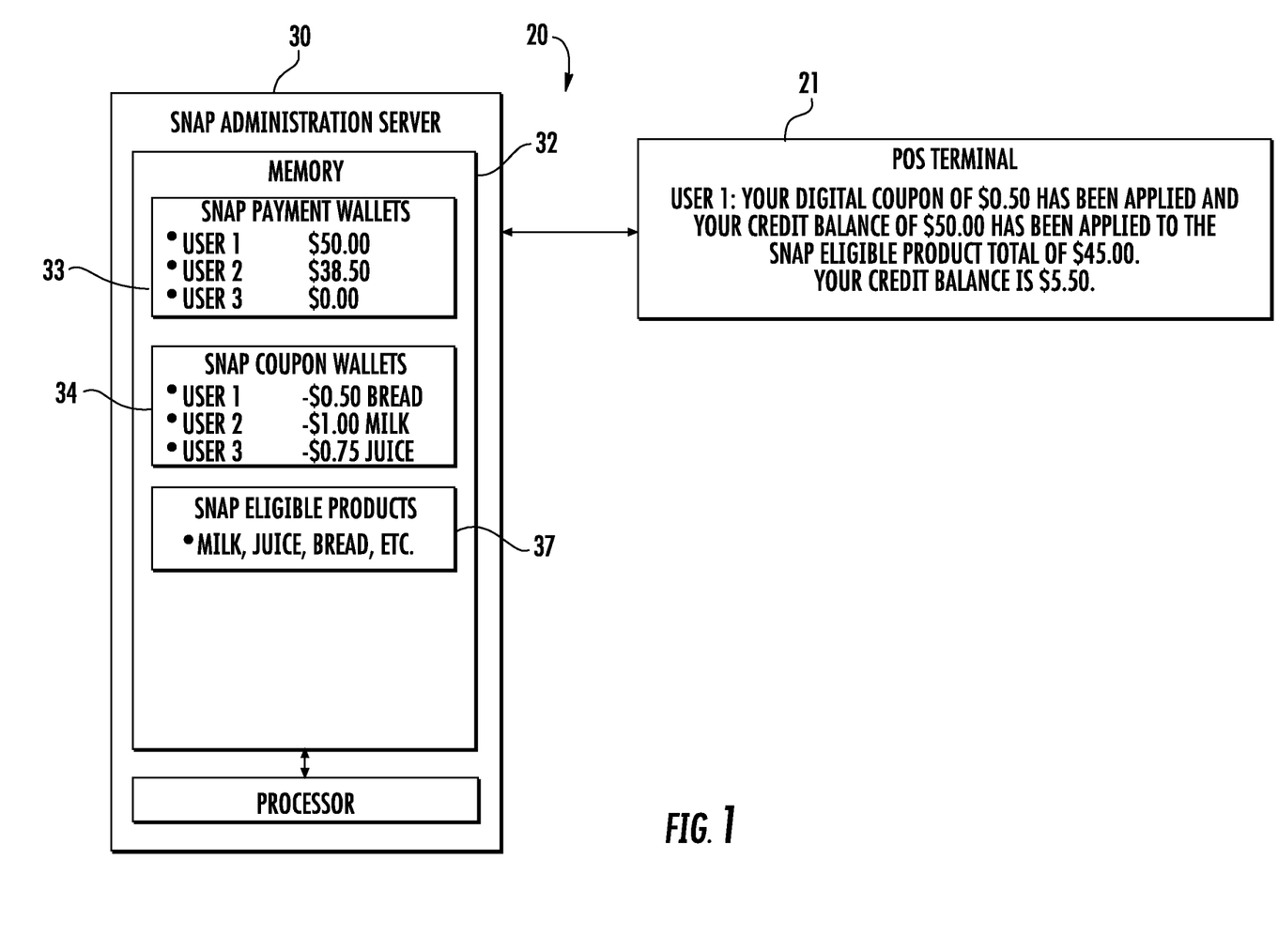
FIG. 1 is a schematic diagram of a system according to an embodiment.
Figure 2:
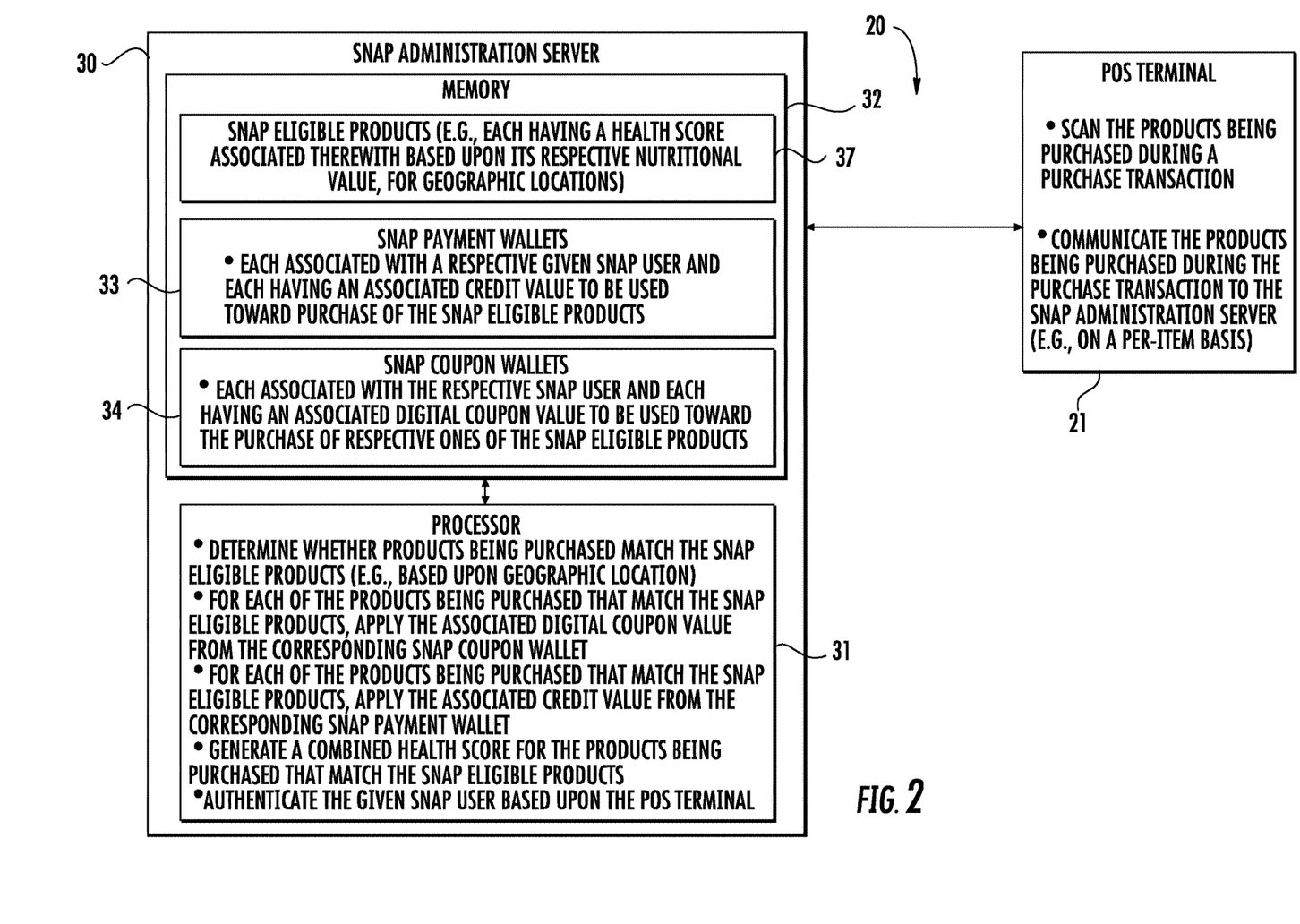
FIG. 2 is a schematic block diagram of the system of FIG. 1.
Figure 3:
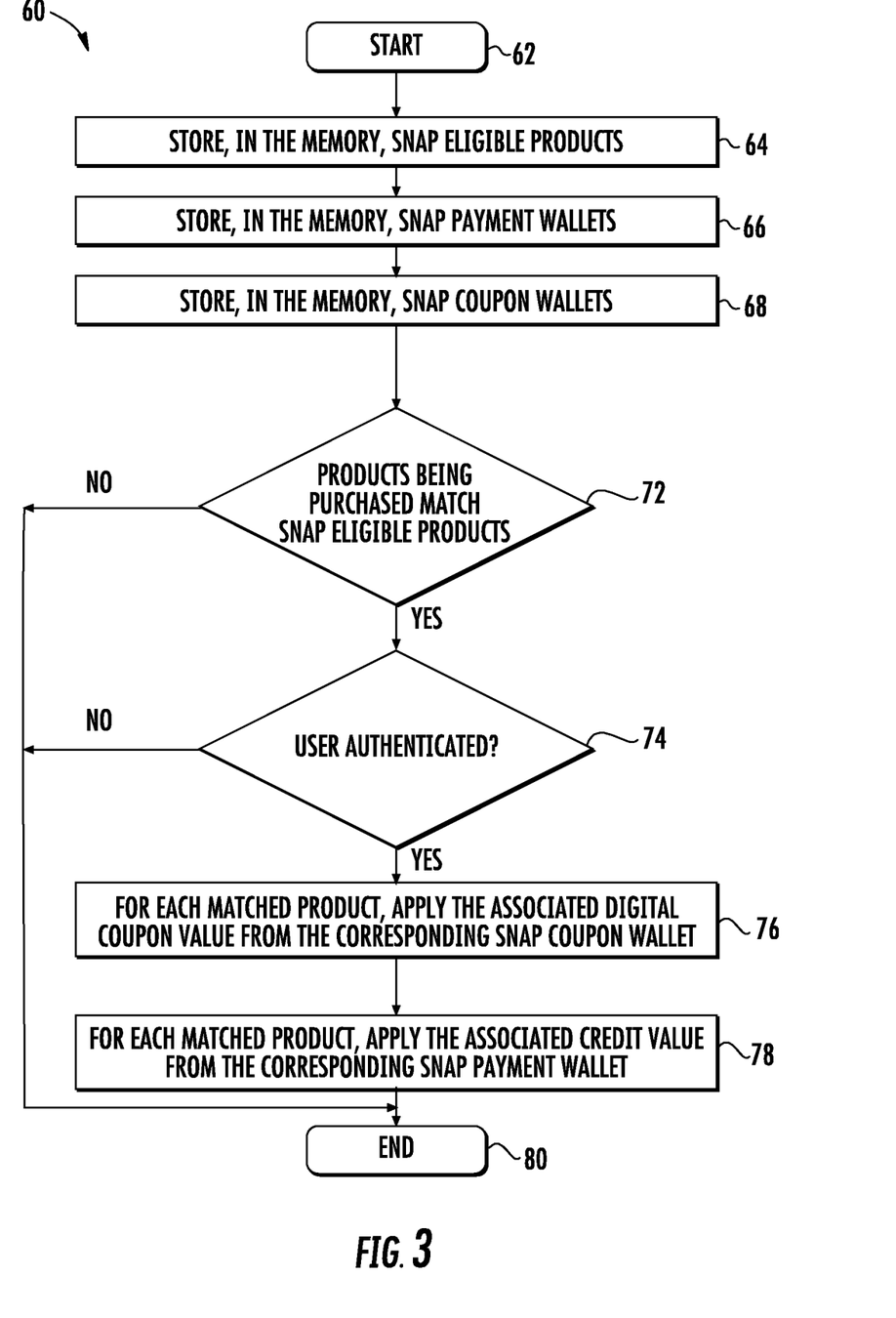
FIG. 3 is a flowchart of a method of processing a SNAP according to an embodiment.

Referring initially to FIGS. 1 and 2, and the flowchart 60 in FIG. 3, a system 20 for processing a supplemental nutrition assistance program (SNAP) illustratively includes a point-of-sale (POS) terminal 21 and a SNAP administration server 30 or SNAP administration service coupled to the POS terminal. The POS terminal 21 scans products being purchased during a purchase transaction and communicates the products being purchased during the purchase transaction to the SNAP administration server 30. In some embodiments, the POS terminal 21 communicates the products on a per-item or per-scan basis so that the SNAP administration server 30 knows all the products being purchased as they are being purchased (e.g., in real time). The POS terminal 21 may additionally or alternatively communicate all the products (i.e., the entire basket including all products therein) after all the products have been scanned (i.e., a per-basket basis).

Beginning at Block 62, the SNAP administration server 30 includes a processor 31 and a memory 32, for example, a database, cooperating therewith to store, in the memory 32, SNAP eligible products 37 (Block 64). SNAP eligible products 37 may include, for example, breads and cereals, fruits and vegetables, meats, fish, and poultry, dairy products, and seeds and plants to grow and produce food for the household to eat. SNAP ineligible products may include beer, wine, liquor, cigarettes, or tobacco, pet food, soaps, paper products, or household supplies, vitamins or other medicines, food that will be eaten in a store, and hot foods, for example. Of course, as will be appreciated by those skilled in the art, SNAP eligible products 37 may vary based upon geographic location, for example, state to state.

The SNAP administration server 30 by way of cooperating of the processor 31 and memory 32, store, in the memory, SNAP payment wallets 33 (Block 66). Each SNAP payment wallet 33 is associated with a respective given SNAP user and each has an associated credit value to be used toward purchase of the SNAP eligible products 37. In other words, the SNAP payment wallet 33 may conceptually be considered an electronic (i.e., not physical) debit card or electronic benefits transfer (EBT) card.

The SNAP administration server 30 also stores, in the memory 32, SNAP coupon wallets 34 each associated with the respective given SNAP user (Block 68). Each SNAP coupon wallet 34 also has an associated digital coupon value to be used toward the purchase of the SNAP eligible products 37. Similar to each SNAP payment wallet 33, each SNAP coupon wallet 34 may conceptually be considered a digital coupon store (i.e., not physical or paper) that may store "clipped" retailer and/or manufacturer supplied digital coupons, for example, for a discount on particular SNAP eligible products 37. Unlike the SNAP payment wallet 33, the digital coupon value of digital coupons stored in the SNAP coupon wallet 34 may be applied to certain SNAP eligible products 37, and not all SNAP eligible products as with the SNAP coupon wallet.

At Block 72, the SNAP administration server 30 determines whether the products being purchased match the SNAP eligible products 37, for example, based upon the geographic location as SNAP eligible products may vary geographically, for example, state to state, as described above. The geographic location may, for example, be determined based upon the POS terminal 21 (e.g., POS terminal identifier, geographic position coordinates, internet or network address, and/or other identifying information that may be used to determine the geographic location). If no products match, the method ends at Block 80.

At Block 74, the SNAP administration server 30 may authenticate the user based upon the POS device 21. For example, the user may enter, at the POS terminal 21, their phone number, loyalty program number, PIN or other identifier that may be used to authenticate the user to both their SNAP payment and coupons wallets 33, 34. Of course, the user may be authenticated based upon other and/or additional techniques, for example, biometrics. If the user is not authenticated, the method ends at Block 80. In some embodiments, the SNAP administration server 30 may not authenticate the given SNAP user.

At Block 76, upon authentication and for each of the products being purchased that match the SNAP eligible products 37, the SNAP administration server 30 applies the associated digital coupon value from the corresponding SNAP coupon wallet. For example, the given user may have a digital coupon for $0.50 off Brand-A bread stored in their SNAP coupon wallet 34. Upon the determination that Brand-A bread is being purchased, the SNAP administration server 30 applies the digital coupon of $0.50 off the cost of the Brand A bread. The digital coupon may apply only to SNAP eligible products 37. However, in some embodiments, the digital coupons may also apply to SNAP ineligible products. In some embodiments, the digital coupons may be credited back to the corresponding SNAP payment wallet 33, for example, after the transaction is complete.

At Block 78, upon authentication and for each of the products being purchased that match the SNAP eligible products 37, the SNAP administration server 30 applies the associated credit value from the corresponding SNAP payment wallet 33 toward the purchase at the POS terminal 21. For example, the given user may have $50 of credit value in their SNAP payment wallet 33 (e.g. provided by a state electronically), which may act like a debit card and be applied to the total purchase. Accordingly, in the above example, if the user has a total purchase of $45 and the $0.50 digital coupon for Brand A bread, the credit value of $50 from their SNAP payment wallet 33 will cover the entire amount with a $5.50 balance. If however, the total purchase exceeds the $50 credit value, for example, $55, the user may be responsible for payment of the difference of $5, e.g., via cash, personal credit/debit card, etc. at the POS terminal 21. The credit value does not apply to SNAP ineligible products. The method ends at Block 80.

In some embodiments, each of the SNAP eligible products 37 may have a health score associated therewith based upon its respective nutritional value. For example, white bread may have a worse or lesser score than whole wheat bread, for example. The SNAP administration server 30 may generate a combined health score for the products being purchased that match the SNAP eligible products 37. For example, a user that purchases healthier SNAP eligible products 37 will obtain a higher or better combined health score, which may be used a basis to provide further incentives, for example, digital coupons, to maintain the relatively healthy food purchasing habits. Digital coupons may be provided to users with combined health scores that may be indicative of less healthy food purchasing habits. In some embodiments, the combined health score may be for an entire basket, that is, for all products being purchased regardless of whether they are SNAP eligible or SNAP ineligible.

Figure 4:
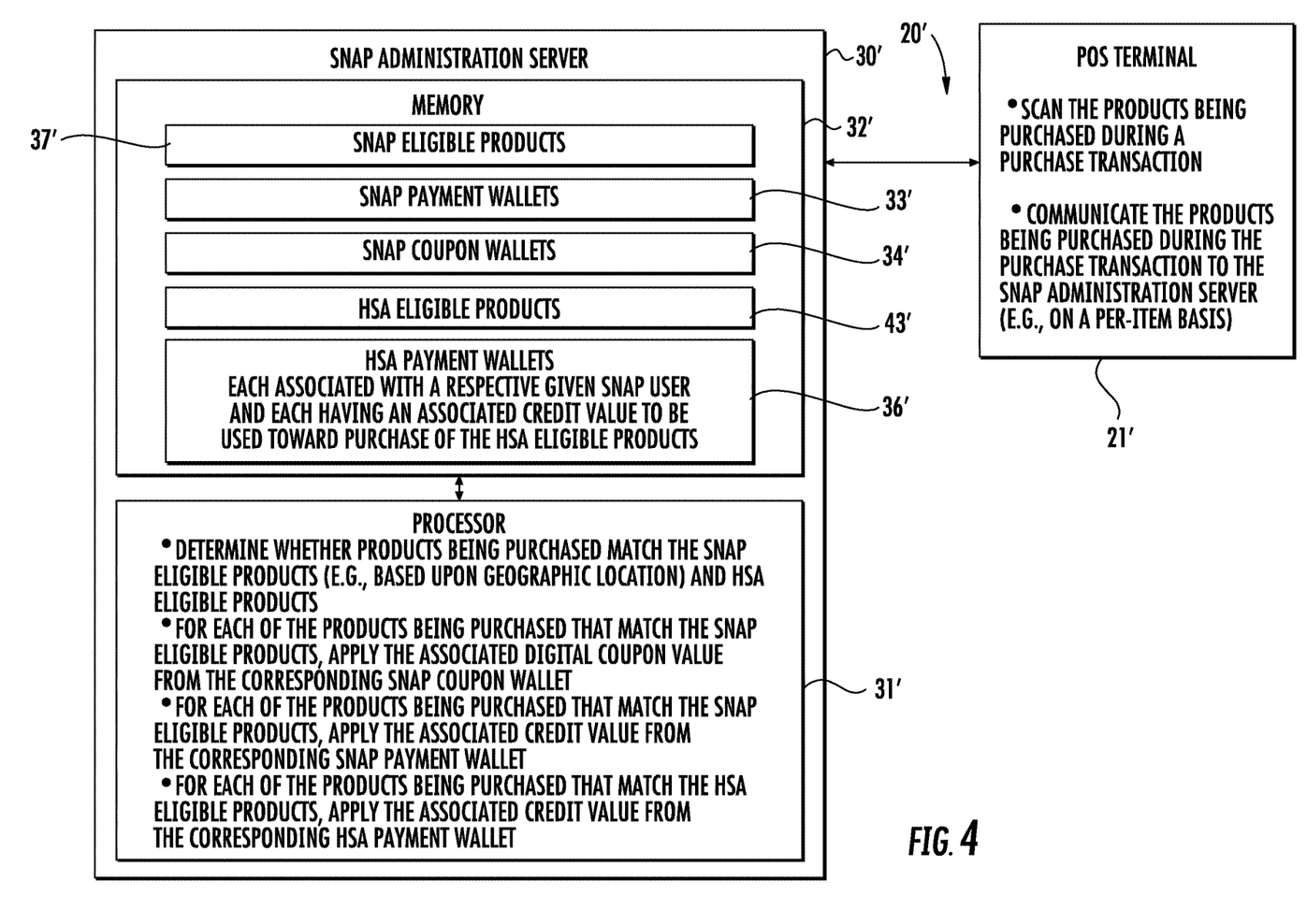
FIG. 4 is a schematic block diagram of a system according to another embodiment.

Referring now to FIG. 4, in some embodiments, the SNAP administration server 30' may store, in the memory 32', Health Savings Account (HSA) eligible products 43' and store, in the memory, HSA payment wallets 36' each associated with a respective given SNAP user and each having an associated HSA credit value to be used toward the purchase of the HSA eligible products 43'. HSA accounts, for example, may be funded from the given user's paycheck or other funding source. The SNAP administration server 30' may also determine whether the products being purchased match the HSA eligible products 43', and for each of the products being purchased that match the HSA eligible products, apply the associated HSA credit value from the corresponding HSA payment wallet 36' toward the purchase at the POS terminal 21'. In other words, HSA eligible products 43' are processed similar to the processing of SNAP eligible products 37' described above. In some embodiments, the HSA eligible products 43' may be processed by another or separate HSA administration server and/or operate independently from the processing of SNAP eligible products 37' as described herein.

Figure 5:
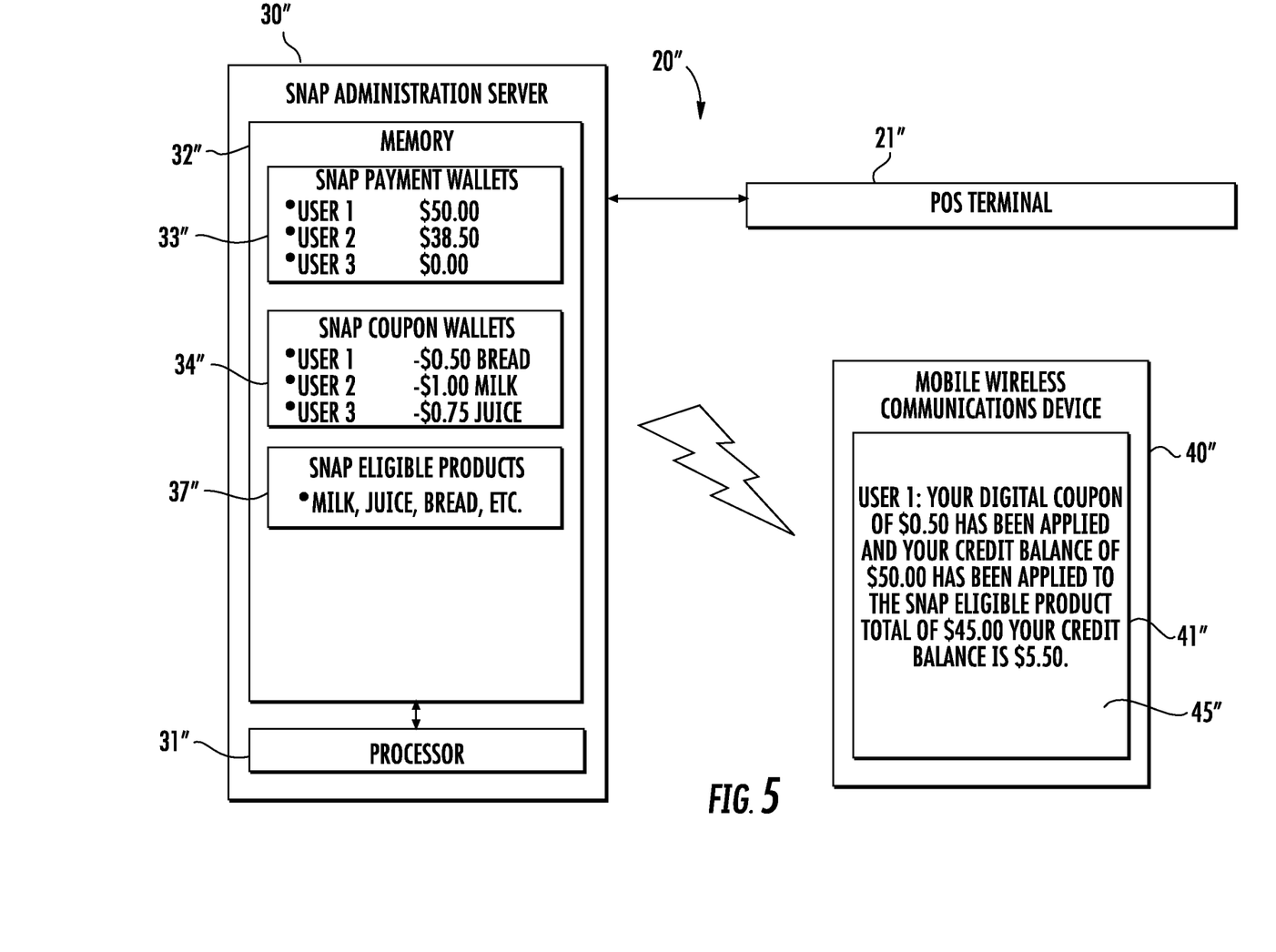
FIG. 5 is a schematic diagram of a system according to another embodiment.
Figure 6:
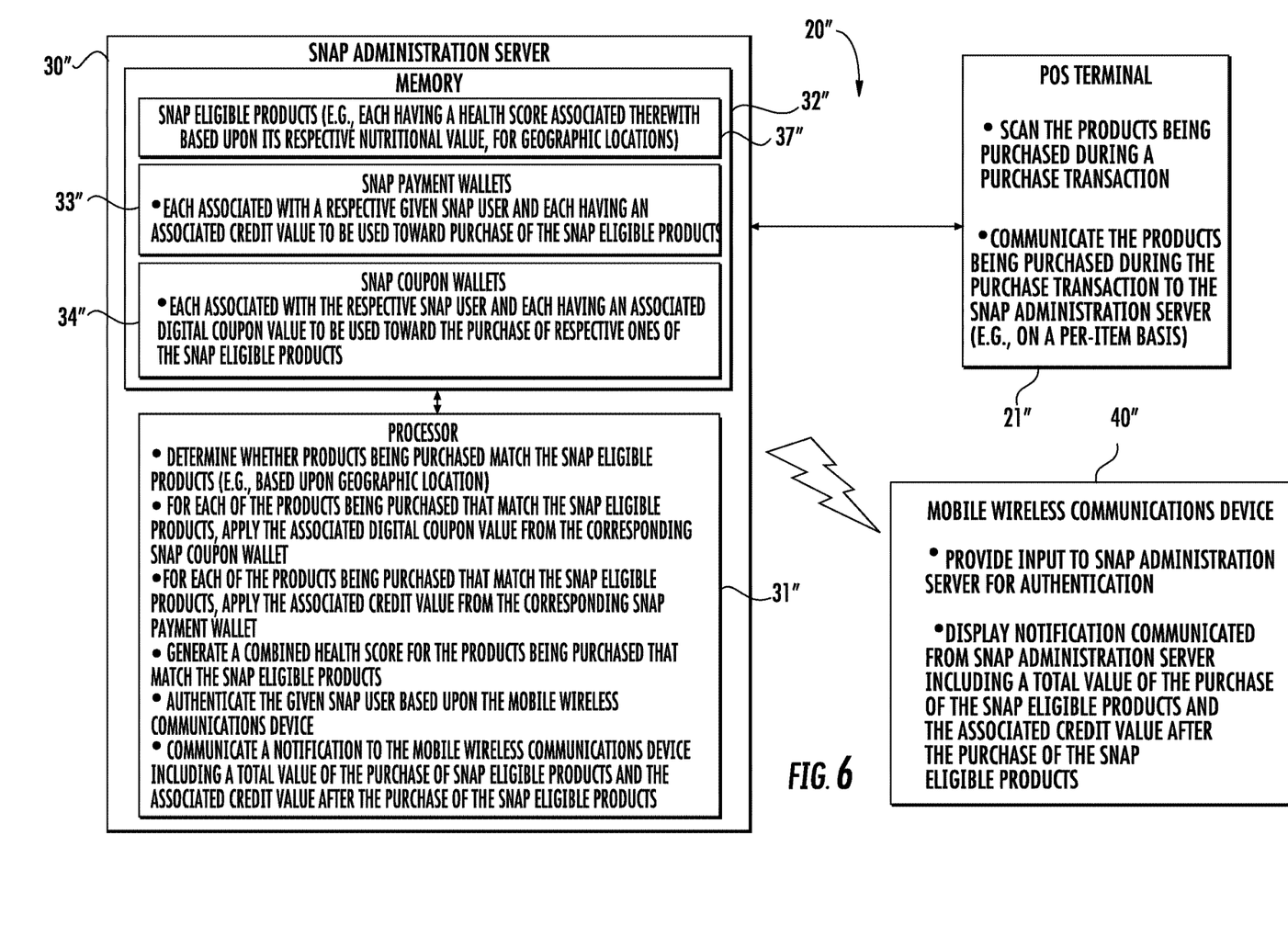
FIG. 6 is a schematic block diagram of the system of FIG. 5.

Referring now to FIGS. 5 and 6, in another embodiment, the system 20" may include a mobile wireless communications device 40" communicating (e.g., wirelessly) with the SNAP administration server 30". The SNAP administration server 30" may authenticate the given SNAP user based upon the mobile wireless communication device 40". For example, based upon user input of a PIN or other unique user identifier and/or based upon a user biometric (e.g., finger, retina, etc.) acquired at the mobile wireless communications device 40", the SNAP administration server 30" may authenticate the SNAP user. The SNAP administration server 30" may also communicate a notification 45" to the mobile wireless communications device 40" that includes a total value of the purchase of the SNAP eligible products 37" and the associated credit value after the purchase of the SNAP eligible products. The notification 45" may be in the form of a text or SMS message, application notification, or other type of notification displayed on a display 41" of the mobile wireless communications device 40".

As will be appreciated by those skilled in the art, some retailers may not know whether a given product is SNAP eligible and may, unknowingly, permit an ineligible product to be purchased under SNAP. In some cases, a retailer may be complicit in permitting the purchase of ineligible SNAP products. The system 20 may advantageously reduce fraud by determining, for example, on a state-to-state basis, which products are SNAP eligible and managing the funds or credit to be applied toward the purchase of SNAP eligible products 37. In other words, the system 20 may provide a single administrator for managing the credits, for determining which products are SNAP eligible, and for applying digital coupons. Furthermore, the system 20 may advantageously provide the functions that are typically processed by several discrete computers and entities. Thus, in addition to reducing fraud, processing times are reduced.

A method aspect is directed to a method of processing a supplemental nutrition assistance program (SNAP). The method includes using a SNAP administration server 30 that includes a processor 31 and a memory 32 cooperating therewith to store, in the memory, a SNAP eligible products 37 and store, in the memory, a SNAP payment wallets 33 each associated with a respective given SNAP user and each having an associated credit value to be used toward purchase of the SNAP eligible products. The method also includes using the SNAP administration server 30 to store, in the memory 32, SNAP coupon wallets 34 each associated with the respective given SNAP user and each having an associated digital coupon value to be used toward the purchase of respective ones of the SNAP eligible products 37 and determine products being purchased from a POS terminal 21. The system may also include using the SNAP administration server 30 to determine whether the products being purchased match the SNAP eligible products 37, and, for each of the products being purchased that match the SNAP eligible products, apply the associated digital coupon value from the corresponding SNAP coupon wallet 34 and apply the associated credit value from the corresponding SNAP payment wallet 33 toward the purchase at the POS terminal 21.

A computer readable medium aspect is directed to a non-transitory computer readable medium that includes computer-executable instructions that cause a processor 31 of a supplemental nutrition assistance program (SNAP) administration server 30 to perform operations that include storing, in a memory 32 coupled to the processor, SNAP eligible products 37 and storing, in the memory, SNAP payment wallets 33 each associated with a respective given SNAP user and each having an associated credit value to be used toward purchase of the SNAP eligible products. The operations include storing, in the memory 32, SNAP coupon wallets 34 each associated with the respective given SNAP user and each having an associated digital coupon value to be used toward the purchase of respective ones of the SNAP eligible products 37, determining products being purchased from a POS terminal 21, and determining whether the products being purchased match the SNAP eligible products. The operations also include, for each of the products being purchased that match the SNAP eligible products 37, applying the associated digital coupon value from the corresponding SNAP coupon wallet 34 and applying the associated credit value from the corresponding SNAP payment wallet 33 toward the purchase at the POS terminal 21.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A system for processing a supplemental nutrition assistance program (SNAP) comprising:
   a remote device;
   a point-of-sale (POS) terminal; and
   a SNAP administration server coupled to said remote device and said POS terminal, and comprising a processor and a memory cooperating therewith to
      store, in said memory, a plurality of SNAP eligible products each having an associated nutritional value,
      store, in said memory, a plurality of SNAP payment wallets each associated with a respective given SNAP user and each having an associated credit value to be used toward purchase of the plurality of SNAP eligible products,
      store, in said memory, a plurality of SNAP coupon wallets each associated with the respective given SNAP user and each having an associated digital coupon value to be used toward the purchase of respective ones of the plurality of SNAP eligible products,
      obtain, from said POS terminal, products being purchased during a purchase transaction,
      determine whether the products being purchased match the plurality of SNAP eligible products,
      for each of the products being purchased that match the plurality of SNAP eligible products, apply the associated digital coupon value from the corresponding SNAP coupon wallet and apply the associated credit value from the corresponding SNAP payment wallet toward the purchase at said POS terminal,
      for each of the products being purchased, determine a health score based upon the respective nutritional values,
      determine a combined health score based upon the health score of each of the products being purchased, a higher combined health score being indicative of purchasing healthier SNAP eligible products,
      generate a digital coupon for a SNAP eligible product based upon the combined health score exceeding a threshold indicative of less healthy food purchasing habits, the digital coupon providing incentive to increase the combined health score, and
      communicate a notification to said remote device including a total value of the purchase of the plurality of SNAP eligible products and the associated credit value after the purchase of the plurality of SNAP eligible products.

2. The system of claim 1 wherein said POS terminal is configured to scan the products being purchased during a purchase transaction.

3. The system of claim 2 wherein said POS terminal is configured to communicate the products being purchased during the purchase transaction to said SNAP administration server.

4. The system of claim 3 wherein said POS terminal is configured to communicate the products being purchased on a per-item basis.

5. The system of claim 1 wherein the plurality of SNAP eligible products are for a plurality of geographic locations; and wherein said processor and said memory cooperate to determine a geographic location of said POS terminal and determine whether the products being purchased match the plurality of SNAP eligible products based upon the geographic location.

6. The system of claim 1 wherein said processor is configured to cooperate with said memory to authenticate the given SNAP user based upon said POS terminal.

7. The system of claim 1 wherein said processor is configured to authenticate the given SNAP user based upon said remote device.

8. The system of claim 1 wherein said remote device comprises a mobile wireless communications device.

9. The system of claim 1 wherein said processor and memory cooperate to:
   store, in said memory, a plurality of Health Savings Account (HSA) eligible products;
   store, in said memory, a plurality of HSA payment wallets each associated with a respective given SNAP user and each having an associated HSA credit value to be used toward purchase of the plurality of HSA eligible products;
   determine whether the products being purchased match the plurality of HSA eligible products; and
   for each of the products being purchased that match the plurality of HSA eligible products, apply the associated HSA credit value from the corresponding HSA payment wallet toward the purchase at said POS terminal.

10. A supplemental nutrition assistance program (SNAP) administration server comprising:
    a memory; and
    a processor coupled to said memory and configured to
       store, in said memory, a plurality of SNAP eligible products each having an associated nutritional value,
       store, in said memory, a plurality of SNAP payment wallets each associated with a respective given SNAP user and each having an associated credit value to be used toward purchase of the plurality of SNAP eligible products,
       store, in said memory, a plurality of SNAP coupon wallets each associated with the respective given SNAP user and each having an associated digital coupon value to be used toward the purchase of respective ones of the plurality of SNAP eligible products,
       obtain, from a point-of-sale (POS) terminal, products being purchased during a purchase transaction,
       determine whether the products being purchased match the plurality of SNAP eligible products,
       for each of the products being purchased that match the plurality of SNAP eligible products, apply the associated digital coupon value from the corresponding SNAP coupon wallet and apply the associated credit value from the corresponding SNAP payment wallet toward the purchase at the POS terminal,
       for each of the products being purchased, determine a health score based upon the respective nutritional values, determine a combined health score based upon the
health score of each of the products being purchased,
a higher combined health score being indicative of
purchasing healthier SNAP eligible products, generate a digital coupon for a SNAP eligible product
based upon the combined health score exceeding a
threshold indicative of less healthy food purchasing
habits, the digital coupon providing incentive to
increase the combined health score, and communicate a notification to a remote device including a total value of the purchase of the plurality of SNAP eligible products and the associated credit value after the purchase of the plurality of SNAP eligible products.

11. The SNAP administration server of claim 10 wherein the plurality of SNAP eligible products are for a plurality of geographic locations; and wherein said processor and memory cooperate to determine a geographic location of said POS terminal and determine whether the products being purchased match the plurality of SNAP eligible products based upon the geographic location.

12. The SNAP administration server of claim 10 wherein said processor is configured to cooperate with said memory to authenticate the given SNAP user based upon the POS terminal.

13. A method of processing a supplemental nutrition assistance program (SNAP) comprising:
using a SNAP administration server comprising a processor and a memory cooperating therewith to
store, in the memory, a plurality of SNAP eligible products each having an associated nutritional value,
store, in the memory, a plurality of SNAP payment wallets each associated with a respective given SNAP user and each having an associated credit value to be used toward purchase of the plurality of SNAP eligible products,
store, in the memory, a plurality of SNAP coupon wallets each associated with the respective given SNAP user and each having an associated digital coupon value to be used toward the purchase of respective ones of the plurality of SNAP eligible products,
obtain, from a point-of-sale (POS) terminal, products being purchased during a purchase transaction,
determine whether the products being purchased match the plurality of SNAP eligible products,
for each of the products being purchased that match the plurality of SNAP eligible products, apply the associated digital coupon value from the corresponding SNAP coupon wallet and apply the associated credit value from the corresponding SNAP payment wallet toward the purchase at the POS terminal,
for each of the products being purchased, determine a health score based upon the respective nutritional values,
determine a combined health score based upon the health score of each of the products being purchased, a higher combined health score being indicative of purchasing healthier SNAP eligible products,
generate a digital coupon for a SNAP eligible product based upon the combined health score exceeding a threshold indicative of less healthy food purchasing habits, the digital coupon providing incentive to increase the combined health score, and
communicate a notification to a remote device including a total value of the purchase of the plurality of SNAP eligible products and the associated credit value after the purchase of the plurality of SNAP eligible products.

14. The method of claim 13 wherein the plurality of SNAP eligible products are for a plurality of geographic locations; and wherein the SNAP administration server is used to determine a geographic location of the POS terminal and determine whether the products being purchased match the plurality of SNAP eligible products based upon the geographic location.

15. The method of claim 13 wherein the SNAP administration server is used to authenticate the given SNAP user based upon the POS terminal.

16. The method of claim 13 wherein the SNAP administration server is used to authenticate the given SNAP user based upon the remote device communicating with the SNAP administration server.

17. The method of claim 13 wherein the remote device comprises a mobile wireless communications device.

18. A non-transitory computer readable medium comprising computer-executable instructions that cause a processor of a supplemental nutrition assistance program (SNAP) administration server to perform operations comprising:
storing, in the memory, a plurality of SNAP eligible products each having an associated nutritional value;
storing, in the memory, a plurality of SNAP payment wallets each associated with a respective given SNAP user and each having an associated credit value to be used toward purchase of the plurality of SNAP eligible products;
storing, in the memory, a plurality of SNAP coupon wallets each associated with the respective given SNAP user and each having an associated digital coupon value to be used toward the purchase of respective ones of the plurality of SNAP eligible products;
obtaining, from a point-of-sale (POS) terminal, products being purchased during a purchase transaction,
determining whether the products being purchased match the plurality of SNAP eligible products;
for each of the products being purchased that match the plurality of SNAP eligible products, applying the associated digital coupon value from the corresponding SNAP coupon wallet and applying the associated credit value from the corresponding SNAP payment wallet toward the purchase at the POS terminal;
for each of the products being purchased, determining a health score based upon the respective nutritional values,
determining a combined health score based upon the health score of each of the products being purchased, a higher combined health score being indicative of purchasing healthier SNAP eligible products;
generating a digital coupon for a SNAP eligible product based upon the combined health score exceeding a threshold indicative of less healthy food purchasing habits, the digital coupon providing incentive to increase the combined health score, and
communicating a notification to a remote device including a total value of the purchase of the plurality of SNAP eligible products and the associated credit value after the purchase of the plurality of SNAP eligible products.

19. The non-transitory computer readable medium of claim 18 wherein the plurality of SNAP eligible products are for a plurality of geographic locations; and wherein the operations comprise determining a geographic location of the POS terminal and determine whether the products being purchased match the plurality of SNAP eligible products based upon the geographic location.

20. The non-transitory computer readable medium of claim 18 wherein the operations comprise authenticating the given SNAP user based upon the POS terminal.

21. The non-transitory computer readable medium of claim 18 wherein the operations comprise authenticating the given SNAP user based upon the remote device communicating with the SNAP administration server.

22. The non-transitory computer readable medium of claim 18 wherein the remote device comprises a mobile wireless communications device.

\* \* \* \* \*